United States Patent [19]

Noda et al.

[11] Patent Number: 5,115,261

[45] Date of Patent: May 19, 1992

[54] PHOTOGRAPHING LIGHT QUANTITY CONTROLLER FOR ENDOSCOPE

[75] Inventors: Nobuhiro Noda; Katsuhiko Furuya; Tadashi Takahashi; Masaaki Nakasima, all of Tokyo, Japan

[73] Assignee: Asahi Kogaku Kogyo Kabushiki Kaisha, Tokyo, Japan

[21] Appl. No.: 553,610

[22] Filed: Jul. 18, 1990

[30] Foreign Application Priority Data

Jul. 25, 1989 [JP] Japan .................................. 1-193684
Oct. 16, 1989 [JP] Japan .................................. 1-270081

[51] Int. Cl.[5] .............................................. G03B 29/00
[52] U.S. Cl. ........................................... 354/62; 362/4
[58] Field of Search ...................... 354/62; 355/68, 69, 355/71; 362/4, 5, 276

[56] References Cited

U.S. PATENT DOCUMENTS

| | | | |
|---|---|---|---|
| 3,680,457 | 8/1972 | Uno et al. | 354/415 |
| 4,021,663 | 5/1977 | Takahashi | 250/227.2 |
| 4,086,583 | 4/1978 | Takahashi | 354/62 |
| 4,153,356 | 5/1979 | Hama | 354/62 |
| 4,322,129 | 3/1982 | Takahashi et al. | 350/269 |
| 4,366,529 | 12/1982 | Takahashi et al. | 362/4 |
| 4,945,366 | 7/1990 | Hisamichi et al. | 354/62 |

FOREIGN PATENT DOCUMENTS 57-26127 6/1982 Japan .
60-51896 11/1985 Japan .
61-36928 8/1986 Japan .

Primary Examiner—L. T. Hix
Assistant Examiner—Howard B. Blankenship
Attorney, Agent, or Firm—Sandler, Greenblum & Bernstein

[57] ABSTRACT

A photographing light quantity controller for an endoscope, which is used to control the quantity of illuminating light when a photograph is to taken through the endoscope. The controller includes a device for photoelectrically converting a brightness level of the reflected light from an object, which is illuminated with a light source, into an electric signal and outputting the signal; a device for integrating an output from the photoelectric conversion device and outputting an integral state value; a device for differentially detecting and outputting the rise of a signal representative of an integral state value which is outputted from the integration device; and a device for controlling the brightness of illuminating light in such a manner that, when the output from the differentially detecting device is greater than a first reference value, the brightness of light that illuminates the object is reduced, whereas, when the output from the differentially detecting device is less than a second reference value which is smaller than the first reference value, the brightness of the illuminating light is increased, and when the output from the differentially detecting device is between the first and second reference value, the brightness of the illuminating light is controlled to a predetermined level between the two brightness levels.

18 Claims, 13 Drawing Sheets

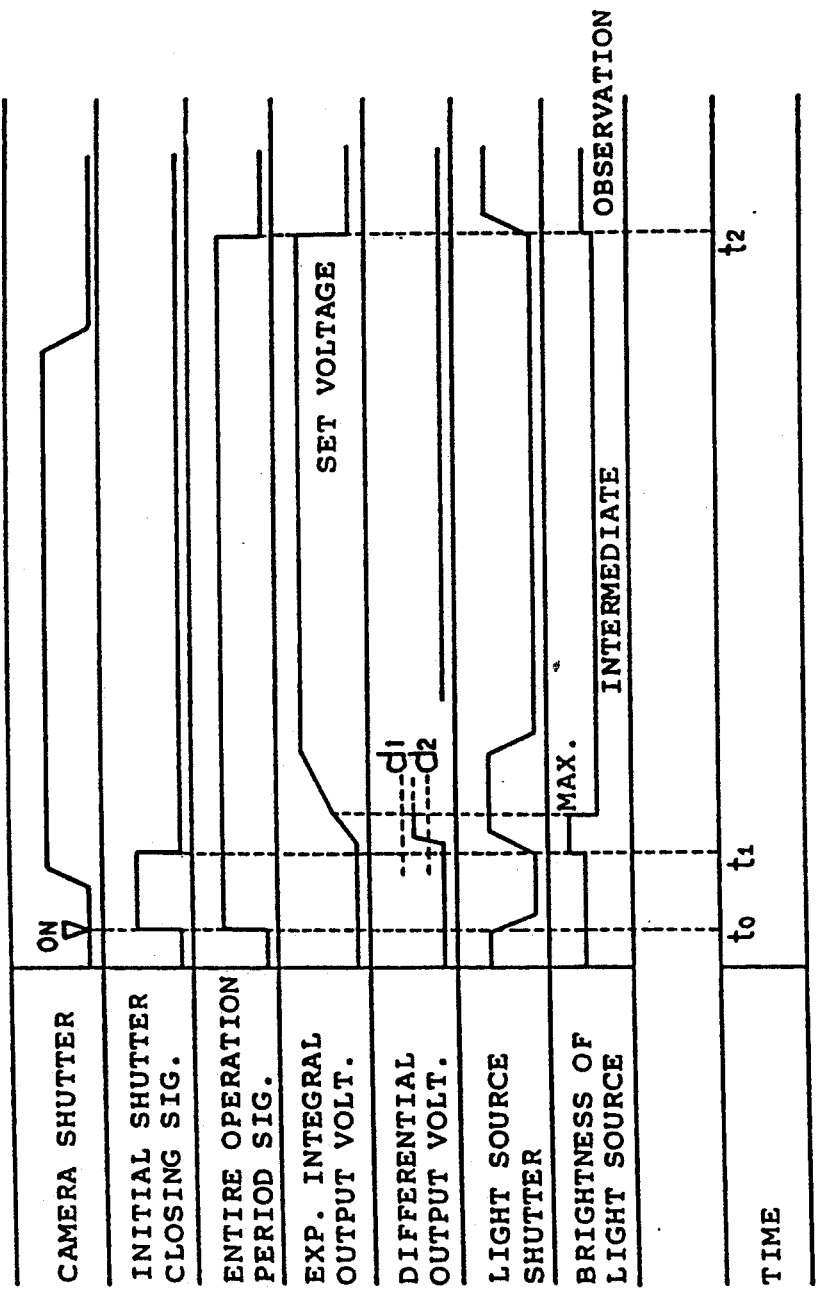

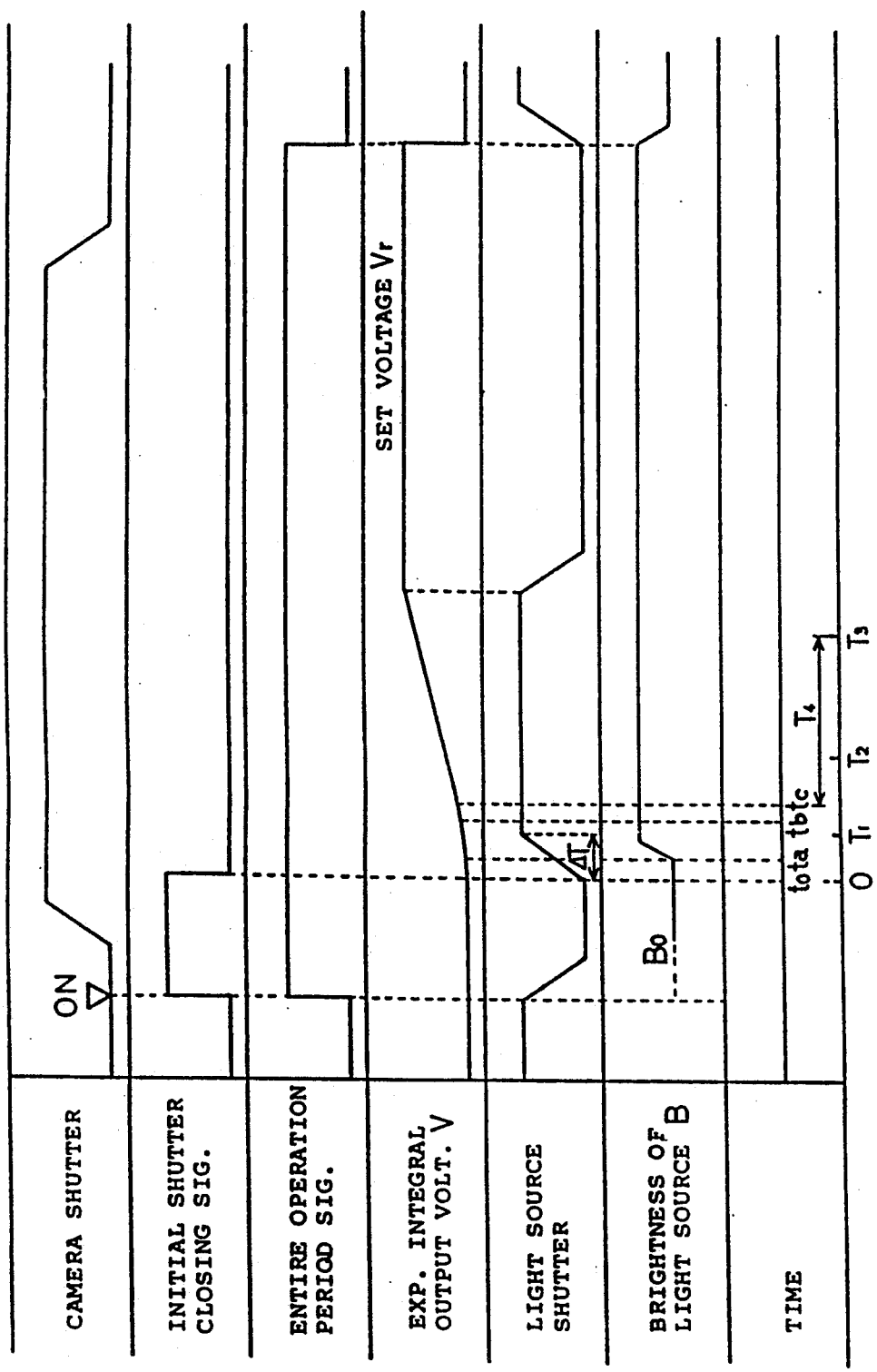

PHOTOGRAPHING LIGHT QUANTITY CONTROLLER FOR ENDOSCOPE

BACKGROUND OF THE INVENTION

1. Field of the Invention

The present invention relates to a photographing light quantity controller for an endoscope, which is used to control the quantity of illuminating light when a photograph is to be taken through the endoscope.

Endoscopes are generally designed to be capable not only of observing the inside of a hollow organ in the patient's body but also of taking a photograph of it. The exposure time for the photography has heretofore been controlled by integrating the output of a light-receiving element which receives the reflected light from an object that is illuminated with a light source device, and closing a mechanical shutter, which is provided in an illuminating light path inside the light source device, when the integral output voltage reaches a set voltage.

However, such a mechanical shutter takes a time from the instant it receives a signal for closing until it has been completely closed (about 0.05 seconds in general), and the exposure therefore becomes correspondingly excessive. The exposure time $\Delta T$ that corresponds to an excess of exposure is constant independent of the length of the overall exposure time on each particular occasion. Accordingly, when the overall exposure time T is relatively short, that is, when the object is relatively bright as in the case of close-up photography, the effect of $\Delta T$ becomes significant, resulting in a high degree of over-exposure.

2. Description of the Background and Relevant Materials

To reduce the degree of over-exposure, a method has heretofore been employed in which the rise of a signal representative of an integral state value which is obtained by integrating the output of a light-receiving element is detected differentially. When the differential output value is greater than a reference value, the brightness of a light source is lowered to an observational state level to increase the overall exposure time T, thereby reducing the effect of $\Delta T$.

In such a device, the lower the reference value, the wider the range within which the degree of over-exposure can be reduced. However, as the reference value lowers, the exposure time lengthens, causing the problem of blur. The reference value must therefore be set at a relatively high level. In consequence, considerable over-exposure still occurs in an intermediate distance range within which the differential output is lower than the reference value.

SUMMARY OF THE INVENTION

An object of the present invention is to provide a photographing light quantity controller for an endoscope, which is capable of preventing both over-exposure and blur when photography is carried out, and capable of obtaining clear, non-blurred pictures, on the whole.

Other objects and advantages of the present invention will become apparent from the following detailed description of an illustrated embodiment of the invention.

According to one embodiment of the present invention, there is provided a photographing light quantity controller for an endoscope, which is used to control the quantity of illuminating light when a photograph is to be taken through the endoscope, comprising: a device for photoelectrically converting a brightness level of the reflected light from an object, which is illuminated with a light source, into an electric signal and outputting the signal; a device for integrating an output from the photoelectric conversion device and outputting an integral value; a device for differentially detecting and outputting the rise of a signal representative of a integral value which is outputted from the integration device; and a device for controlling the brightness of illuminating light in such a manner that, when the output from the differentiation device is higher than a first reference value, the brightness of light that illuminates the object is controlled to a relatively low level, whereas, when the output from the differentiation device is lower than a second reference value which is smaller than the first reference value, the brightness of the illuminating light is controlled to a relatively high level, and when the output from the differentiation device is between the first and second reference values, the brightness of the illuminating light is controlled to a predetermined level between the two brightness levels.

In another embodiment of the invention, there is provided a photographing light quantity controller for an endoscope, which is used to control the quantity of illuminating light when a photograph is to be taken through the endoscope, comprising: a device for photoelectrically converting a brightness level of exposure light that is applied to a photographic plane in a photographing device after being reflected from an object, which is illuminated with a light source, into an electric signal and outputting the signal; a device for integrating an output from the photoelectric conversion device and outputting an integral value; a device for detecting a rate of change per unit time of the output from the integration device and calculating an expected exposure time from the detected value; and a control device which is activated by the output from the expected exposure time calculating device to control the brightness of illuminating light that is supplied from the light source to the endoscope so that the exposure time at the photographic plane falls within a predetermined range.

BRIEF DESCRIPTION OF THE DRAWINGS

The present invention may be more fully understood from the description of a preferred embodiment of the invention set forth below, together with the accompanying drawings, in which:

FIGS. 2a, 2b to 2c are time charts showing the operation of the embodiment of FIGS. 1a and 1b;

FIG. 5 is a time chart showing the operation of the second embodiment;

DESCRIPTION OF THE EMBODIMENT

Figure 1A:
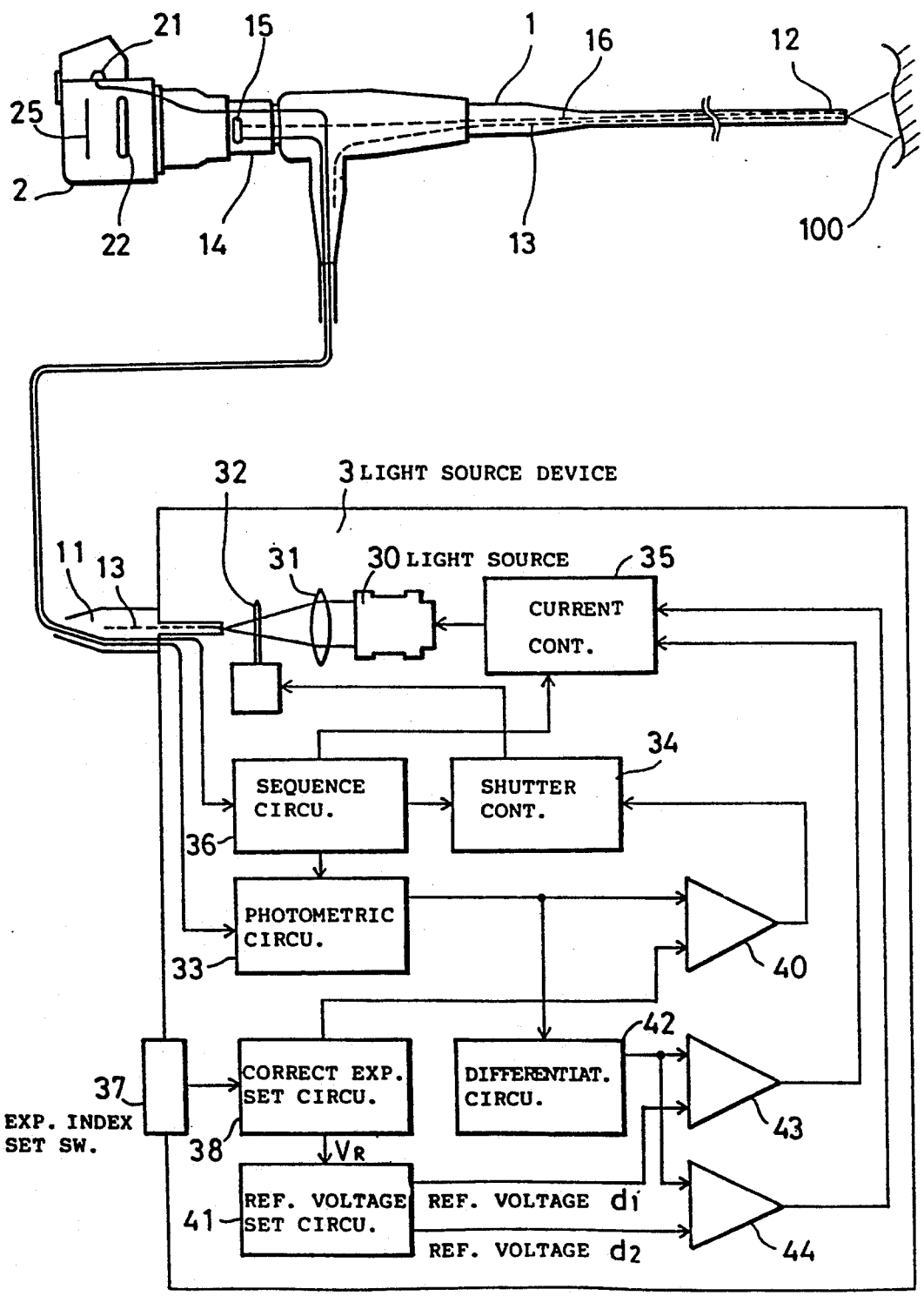
FIGS. 1a and 1b are circuit diagrams of one embodiment of the present invention.

Referring to FIG. 1a, reference numeral 1 denotes an endoscope. A photographing device 2 is detachably attached to the endoscope 1. Reference numeral 3 denotes a light source device for the endoscope 1.

In this system, light from a light source 30, which may be a lamp which is provided in the light source device 3 is transmitted from a connector 11 of the endoscope 1 to the distal end 12 of an insert part of the endoscope 1 through a light guide fiber bundle 13 to illuminate an object 100 in a hollow organ of the patient's body.

The reflected light from the object 100 is transmitted from the insert part distal end 12 to an eyepiece 14 through an image guide fiber bundle 16 for transmitting an image of the object 100. The transmitted light is received by a light-receiving element 15 which is provided in the eyepiece 14, and the level of brightness of the received light is converted into an electric signal and then outputted. Accordingly, the brightness level of the light that reaches the plane of a film 25 is accurately detected and converted into an electric signal.

The light source 30 that is provided in the light source device 3 can be, for example, a xenon lamp. Light that is emitted from the light source 30 is condensed onto the incident end face of the light guide fiber bundle 13 through a condenser lens 31. A mechanical shutter 32 is provided in an illuminating light path which extends between the condenser lens 31 and the light guide fiber bundle 13, so that the illuminating light that enters the light guide fiber bundle 13 can be reduced to zero by closing the shutter 32.

A photometric circuit 33, which is connected to the output end of the light-receiving element 15, integrates the output from the light-receiving element 15 and outputs an integral value. A shutter control circuit 34 controls the opening and closing operation of the shutter 32.

A light source current control circuit 35 controls the current that is supplied to the light source 30 to control the brightness of light emitted from the light source 30. The light source current control circuit 35 enables the brightness of light from the light source 30 to be readily varied between a minimum level and a maximum level.

A synchro switch 21, which is provided on the photographing device 2, is connected to a sequence circuit 36 which is provided in the light source device 3. In response to the ON/OFF operation of the synchro switch 21, the sequence circuit 36 sequentially initiates or terminates the operations of the photometric circuit 33, the shutter control circuit 34 and the light source current control circuit 35.

Reference numeral 37 denotes an exposure index setting switch which is actuated to set an exposure index in conformity to the sensitivity of the film 25 that is employed in the photographing device 2. An exposure index is the index for effecting automatic exposure control in accordance with the sensitivity of the film 25 and other conditions when a photograph is to be taken. In accordance with an exposure index which is inputted through the switch 37, a correct exposure is set in a correct exposure setting circuit 38.

A first comparator 40 compares a value which is outputted from the photometric circuit 33 with a value which is outputted from the correct exposure setting circuit 38 to control the shutter closing operation of the shutter control circuit 34. More specifically, when the output from the photometric circuit 33 rises to reach a value set in the correct exposure setting circuit 38, the shutter 32 is closed.

A reference voltage setting circuit 41 automatically sets a first and second reference voltages $d_1$ and $d_2$ ($d_1 > d_2$) in accordance with a voltage $V_R$ which is outputted from the correct exposure setting circuit 38. The reference voltages $d_1$ and $d_2$ are used as reference values to control the magnitude of current which is supplied to the light source 30.

Figure 1B:
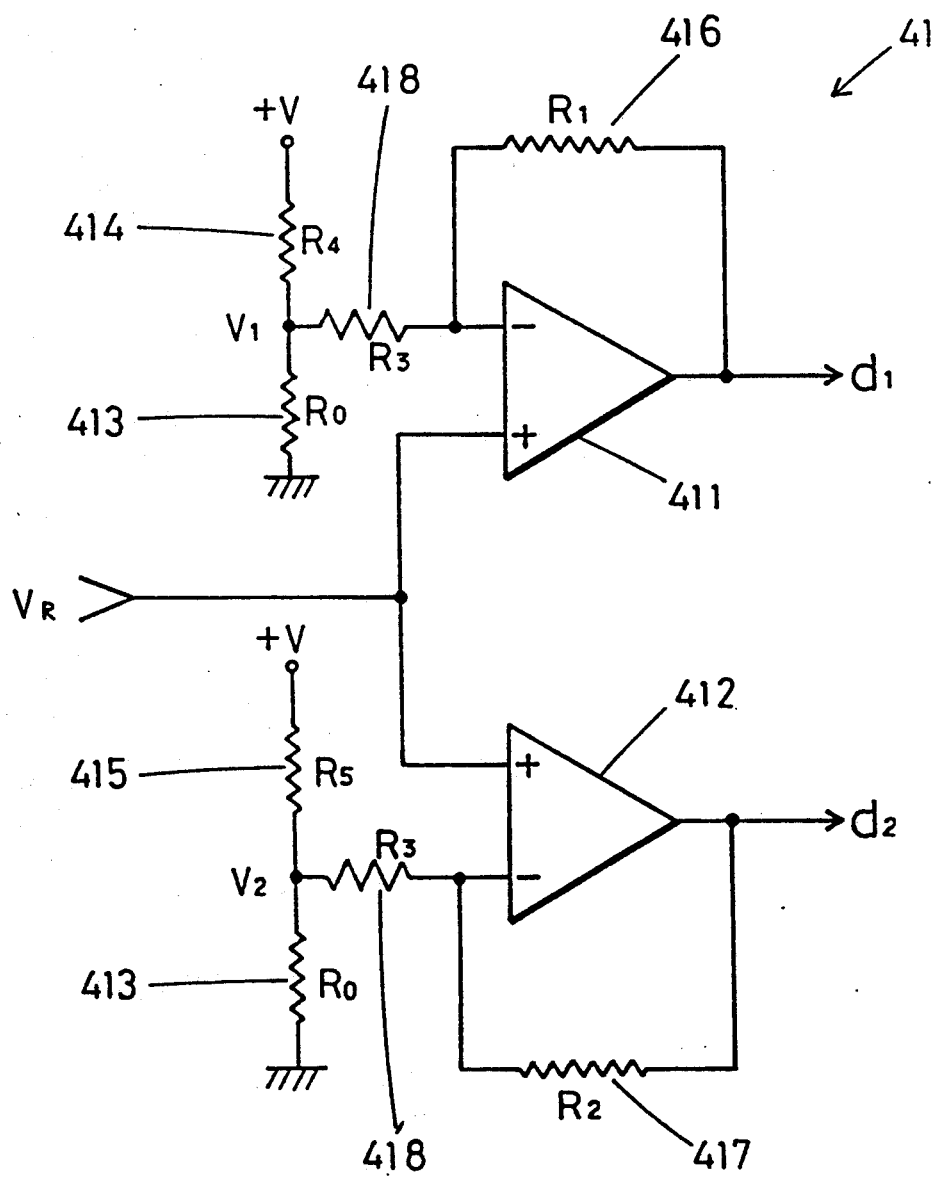

FIG. 1b shows one example of a reference voltage setting circuit 41. In this circuit, the output voltage $V_R$ from the correct exposure setting circuit 38 is inputted to the plus-side input terminal of each of the first and second operational amplifiers 411 and 412.

Reference voltages $V_1$ and $V_2$ are obtained from the power supply voltage V of the apparatus by a first voltage divider that comprises resistors 413 and 414 and a second voltage divider comprising resistors 413 and 415. The two reference potential points are connected to the respective minus-side input terminals of the first and second operational amplifiers 411 and 412 through resistors 418, 418. In addition, feedback resistors 416 and 417 are connected between the output terminals and minus-side input terminals of the operational amplifiers 411 and 412, respectively.

Accordingly, assuming that the resistance values of the resistors 413, 414, 415, 416, 417 and 418 are represented by $R_0$, $R_4$, $R_5$, $R_1$, $R_2$ and $R_3$, respectively, as shown in FIG. 1b, the output (reference) voltages $d_1$ and $d_2$ from the first and second operational amplifiers 411 and 412 are given by $$d_1 = (V_R - V_1)R_1/R_3$$

$$d_2 = (V_R - V_2)R_2/R_3$$

Therefore, if $R_1 > R_2$ and $R_4 = R_5$ (i.e., $V_1 = V_2$), for facilitating the calculation, $$d_1 > d_2$$

If $R_0 << R_3$, the reference voltages $V_1$ and $V_2$ are given by $$V_1 = VR_0/(R_0 + R_4)$$

$$V_2 = VR_0/(R_0 + R_5)$$

where $R_4$ and $R_5$ are set so that both $V_1$ and $V_2$ are smaller than the minimum value of $V_R$.

If, for example, $R_1 = R_3$ and $R_2 = R_3/2$, $$d_1 = 2d_2$$

Thus, the ratio of $d_1$ to $d_2$ becomes favorable for the control of this embodiment. It should be noted that specific sizes of $d_1$ and $d_2$ are determined by taking into consideration the size of the output voltage $V_R$ from the correct exposure setting circuit 38 and the size of the output voltage from the differentiation circuit 42.

In FIG. 1a, the first and second reference voltages $d_1$ and $d_2$ are compared in a second and third comparators 43 and 44, respectively, with an output from a differentiation circuit 42 which differentially detects and outputs the rise of a signal representative of an integral state value that is outputted from the photometric circuit 33. The results of the comparison are sent to the light source current control circuit 35 as follows.

When the output of the differentiation circuit 42 is higher than the first reference voltage $d_1$, the current that is supplied to the light source 30 is controlled to a minimum level to minimize the brightness of light that is emitted from the light source 30 within a variable range.

When the output of the differentiation circuit 42 is lower than the second reference voltage $d_2$, the current that is supplied to the light source 30 is controlled to a maximum level to maximize the brightness of light from the light source 30 within the variable range.

When the output of the differentiation circuit 42 is between the first and second reference voltages $d_1$ and $d_2$, respectively, the current that is supplied to the light source 30 is controlled to a predetermined level between the maximum and minimum levels to set the brightness of light from the light source 30 at an intermediate level.

Figure 2A:
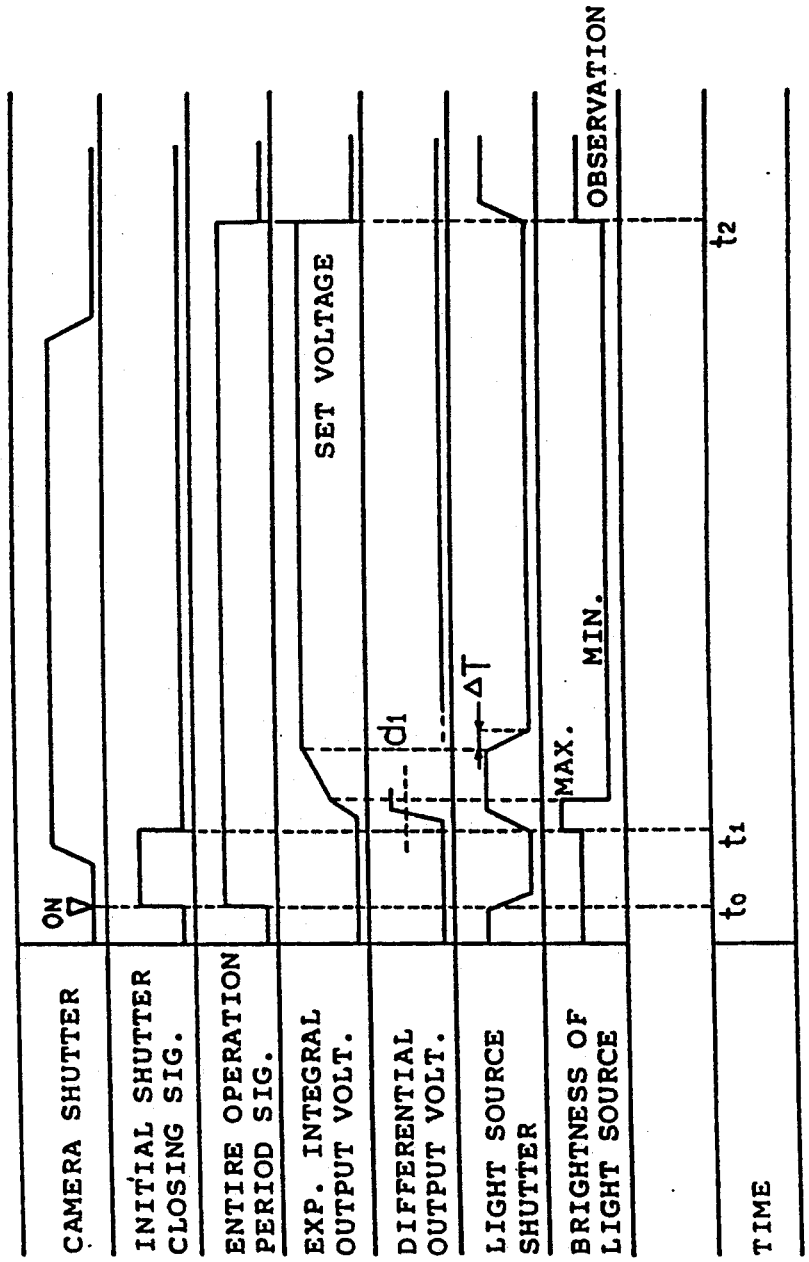
Figure 2B:
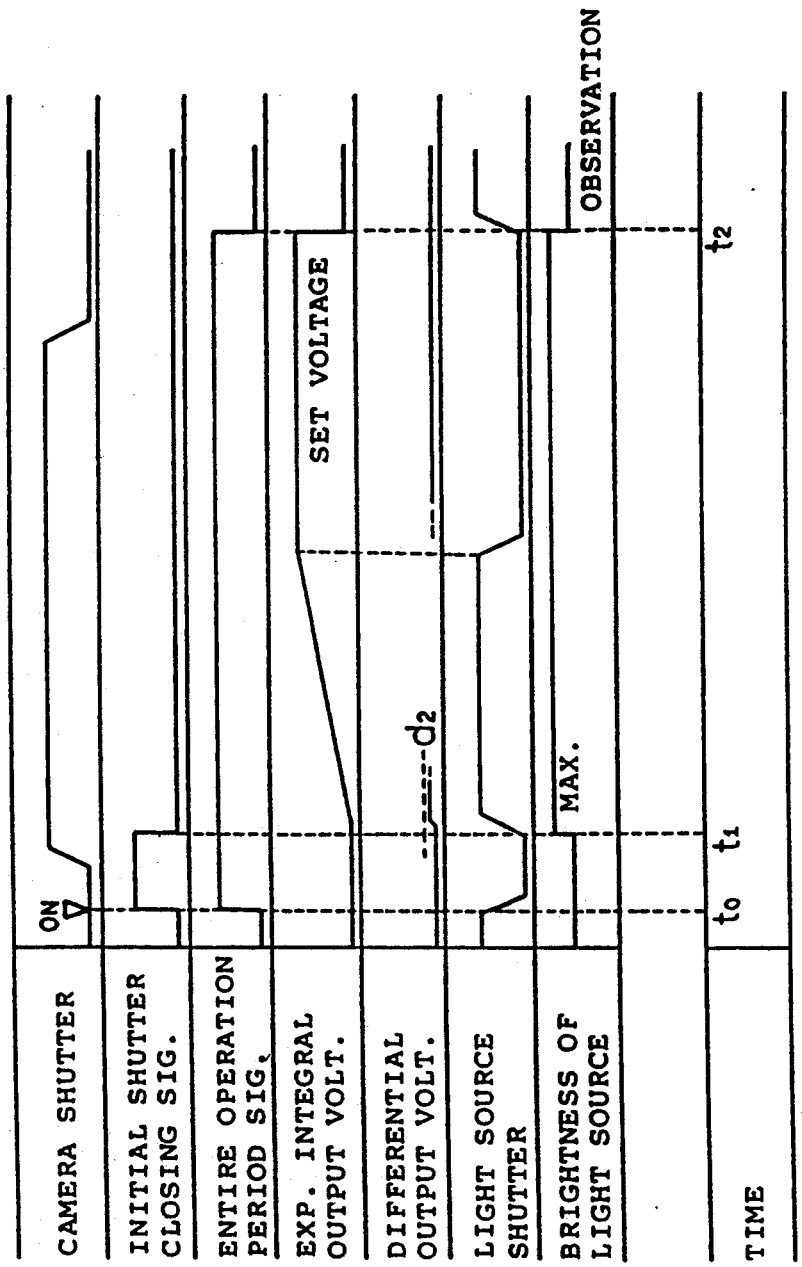

The operation of the above-described embodiment will next be explained with reference to the time charts of FIGS. 2a, 2b and 2c.

When the synchro switch 21 on the photographing device 2 is turned on, the shutter (camera shutter) 22 in the photographing device 2 is opened after a slight delay and is closed after a predetermined time (e.g., 0.25 sec) has elapsed. In the meantime, the shutter 32 in the light source device 3 is temporarily closed in response to a signal which is outputted from the sequence circuit 36 at the same time as the synchro switch 21 is turned on. In addition, an entire operation period signal is turned on. After a relatively short time $t_1$, which is the interval of time between the moment the initial shutter closing signal rises at the same time as the synchro switch 21 is turned on and the moment it falls, the shutter 32 in the light source device 3 is opened. After the camera shutter 22 has been closed and a time $t_2$ has elapsed, the entire operation period signal is turned off (i.e., the entire operation terminates).

At the same time as the initial shutter closing signal falls, the light source shutter 32 begins to open and, at the same time, the brightness of light emitted from the light source 30 is temporarily increased to a maximum level.

When the distance to the object 100 is relatively short, the differential output detected is higher than the first reference voltage $d_1$. In such a case, the brightness of light from the light source 30 lowers to a minimum level within a variable brightness range of light for photography, so that the rise of the integral output voltage becomes slower, resulting in an increase in the length of time needed for the integral output voltage to reach a set level, as shown in FIG. 2a. When the integral output voltage reaches the set level, the light source shutter 32 is closed to terminate the exposure process.

Accordingly, the exposure time becomes longer than in the case where the brightness of light from the light source 30 is left at the maximum level. This longer exposure time results in a reduction in the ratio of the time $\Delta T$, the time required for the shutter 32 to close, to the exposure time. In addition, since the brightness of light from the light source 30 is held at the minimum level during the time $\Delta T$, the degree of overexposure with respect to the plane of the film 25 is reduced.

Conversely, when the distance to the object 100 is relatively long, the differential output detected is lower than the second reference voltage $d_2$. In such a case, the brightness of light from the light source 30 is left at the maximum level, and when the integral output voltage reaches the set level, the light source shutter 32 is closed to terminate the exposure process, as shown in FIG. 2b. Accordingly, the exposure time will not lengthen, and the problem of blurring will not arise.

When the distance to the object 100 is moderate, the differential output detected is intermediate between the first and second reference voltages $d_1$ and $d_2$. In such a case, the brightness of light from the light source 30 is controlled at a predetermined level which is intermediate between the maximum and minimum levels, so that the rise of integral output voltage becomes moderately slow. As a result, the time required for the integral output voltage to reach the set level lengthens to a certain extent, as shown in FIG. 2c. When the integral output voltage reaches the set level, the light source shutter 32 is closed to terminate the exposure process.

Accordingly, the exposure time lengthens to a certain extent, and the degree of over-exposure with respect to the plane of the film 25 is reduced. However, the exposure time will not lengthen as in the case where the brightness of light from the light source 30 is lowered to the minimum level. The problem of blurring will therefore not arise.

It should be noted that, when the differential output is between the first and second reference voltages $d_1$ and $d_2$, the brightness of light from the light source 30 may be controlled at one of a plurality of levels that is selected in conformity with the size of the differential output.

Instead of controlling the brightness of light from the light source 30, the brightness of illuminating light that is applied to the object 100 may be controlled by controlling the aperture of a variable aperture stop which is provided in between the light source 30 and the light guide fiber bundle 13.

According to the present invention, even when the distance to the object is moderate, the exposure time lengthens to a certain extent to prevent occurrence of overexposure. Moreover, since the exposure time will not become as long as in the case where the brightness of light from the light source is controlled to the minimum level within the variable brightness range of light for photography, the problem of blurring will not arise.

Thus, the present invention enables enlargement of the range within which photography can be performed with an ideal exposure time, and hence permits clear photographs to be obtained.

Figure 3:
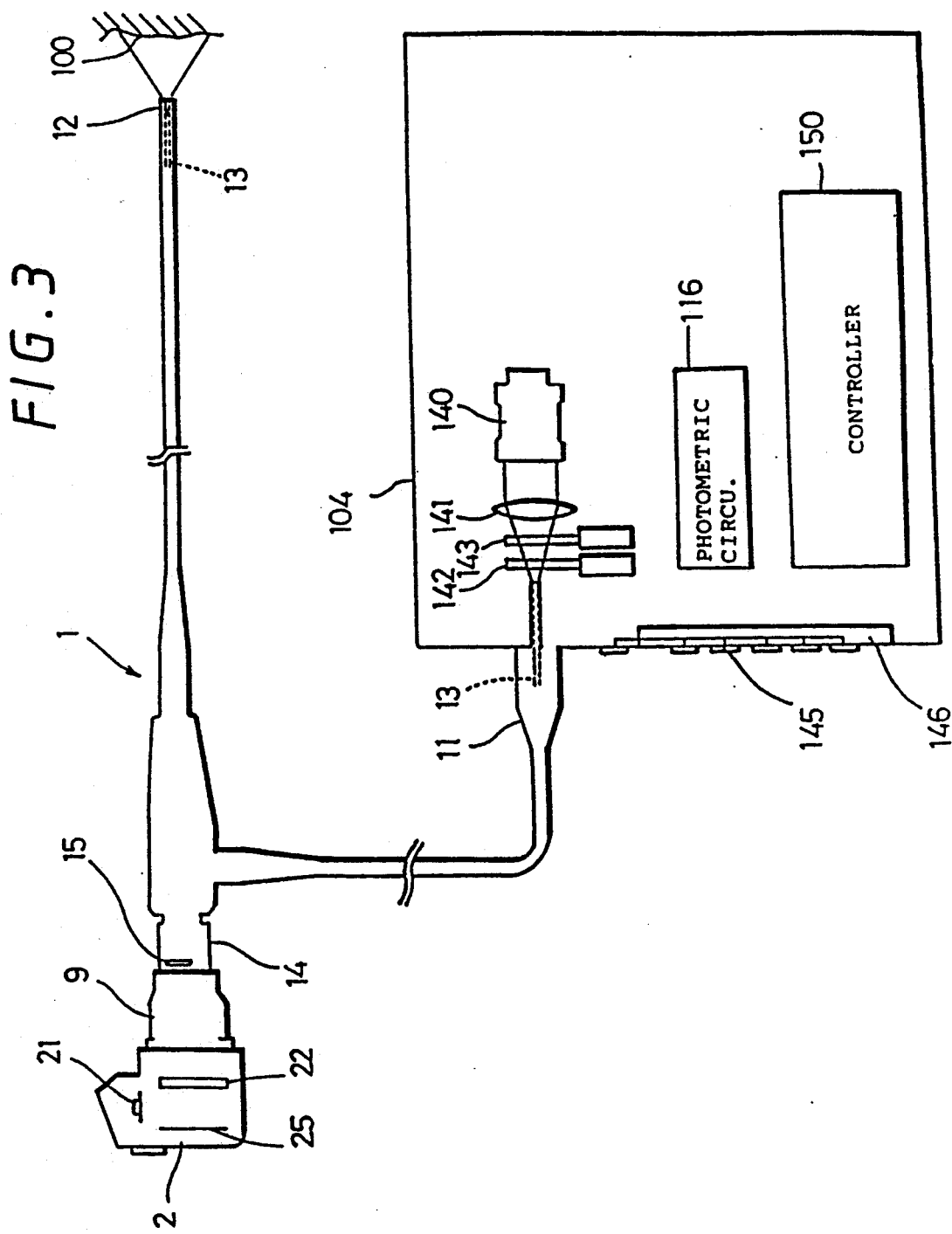
FIG. 3 is a schematic drawings of a second embodiment.

FIG. 3 shows a second embodiment of the present invention. Reference numeral 1 denotes an endoscope. A camera (photographing device) 2 is detachably attached to an eyepiece 14 of the endoscope 1 through an adapter 9.

Reference numeral 104 denotes a light source device, to which is detachably connected a connector 11 of the endoscope 1. Illuminating light that is emitted from a light source 140, which may be a lamp focused through a condenser lens 141 and supplied to a light guide fiber bundle 13 in the endoscope 1.

In an illuminating light path which extends between the light source 140 and the light guide fiber bundle 13 are provided a shutter (light source shutter) 142 which can be opened and closed to fully open and close the illuminating light path, and a diaphragm 143 which is capable of varying the area of passage of the illuminating light.

The illuminating light is transmitted through the light guide fiber bundle 13 and applied to an object 100 from the distal end 12 of an insert part of the endoscope 1. The reflected light from the object 100 is transmitted through an image guide fiber bundle (not shown) to expose the plane (photographic plane) of a film 25 in the camera 2. A shutter (camera shutter) 22 in the camera 2 is opened for a predetermined time (e.g., 0.25 sec) only when a synchro switch 21 is turned on.

A light-receiving element 15 is provided in the eyepiece 14 to convert a brightness level (hereinafter referred to as "luminous flux") of the exposure light that is applied to the plane of the film 25 into an electric signal. The output voltage from the light-receiving element 15 is integrated in a photometric integration circuit 116, and an integral state value is outputted from the photometric circuit 116. The photometric circuit 116 may be provided in either the light source device 104 or the endoscope 1.

Reference numeral 145 denotes an exposure index setting switch which is provided on an operation panel 146 that is attached to the surface of the light source device 104. Reference numeral 150 denotes a controller which incorporates a microcomputer.

Figure 4:
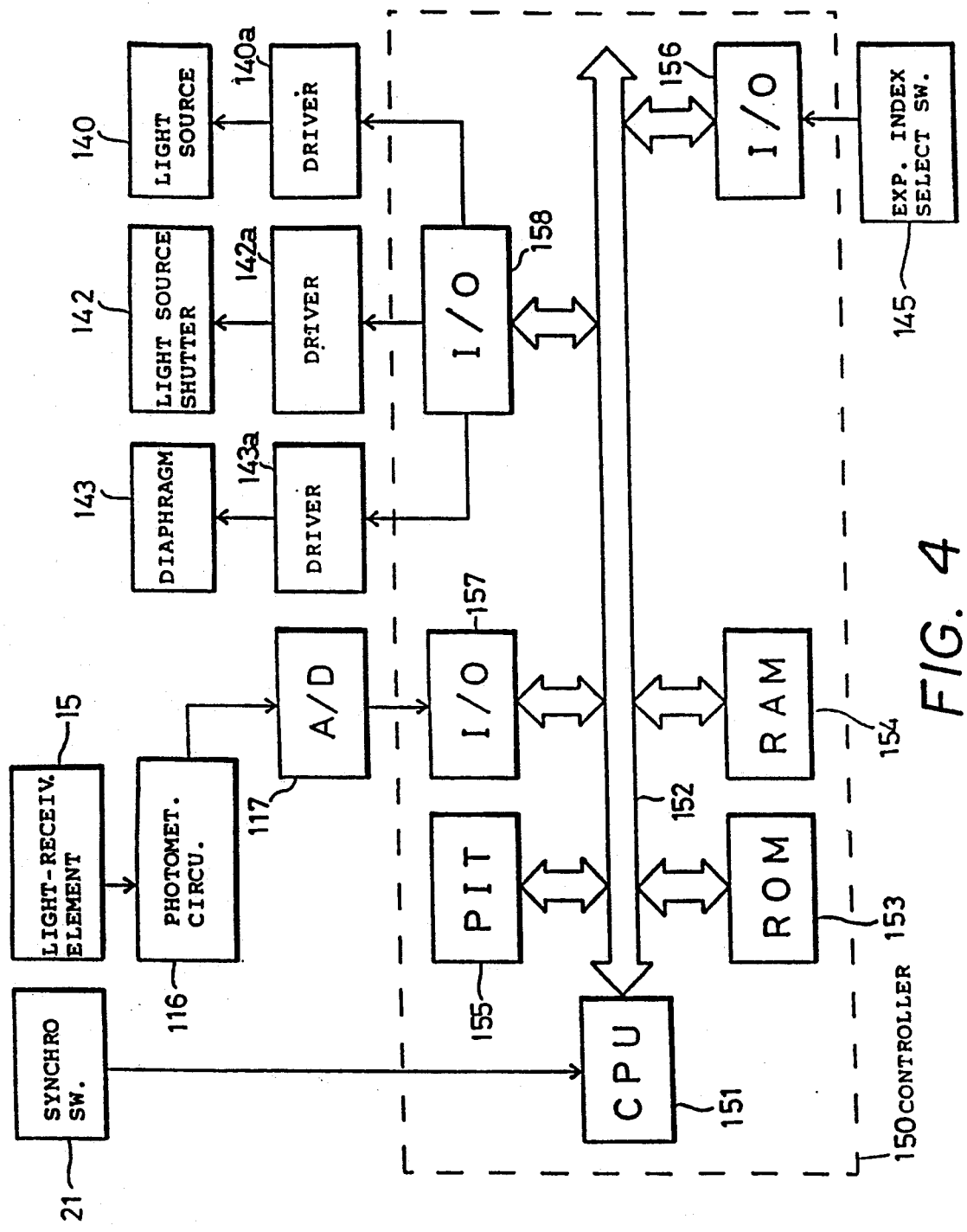
FIG. 4 is a circuit block diagram of the second embodiment.

Referring to FIG. 4, which is a block diagram showing the electrical arrangement of the second embodiment, the controller 150 includes a central processing unit (CPU) 151; and a read only memory (ROM) 153, a random access memory (RAM) 154 and a programmable interval timer (PIT) 155 for counting time elapsed which are connected to the CPU 151 through a system bus 152. The CPU 51 is supplied with an interrupt signal which is outputted from the synchro switch 21.

The system bus 152 is further connected with first, second and third input/output ports 156, 157 and 158, respectively. The exposure index setting switch 145 is connected to the input end of the first input/output port 156. The output from the light-receiving element 15 is integrated in the photometric integration circuit 116 to obtain an integral value (integral output voltage V), which is inputted to the input end of the second input/output port 157 through an analog-to-digital converter 117. The output end of the third input/output port 158 is connected to drivers 140a, 142a and 143a which control the brightness of light emitted from the light source 140, the opening and closing operation of the light source shutter 142, and the degree of opening of the diaphragm 143, respectively.

The system is further provided with an initial shutter closing signal generator which generates a signal for closing the light source shutter 142 for a predetermined, short time in response to the activation of the synchro switch 21, and a signal generator which generates an entire operation period signal that defines the entire operation period of the system in response to the activation of the synchro switch 21. Output signals from these generators are inputted to the controller 150. Illustrations of these generators, however, have been omitted.

FIG. 5 is a time chart showing the operation of the above-described embodiment.

When the synchro switch 21 on the camera 2 is turned on, the shutter (camera shutter) 22 in the camera 2 is opened with a slight delay and is closed after a predetermined time (e.g., 0.25 sec) has elapsed. In the meantime, the light source shutter 142 in the light source device 104 is temporarily closed in response to an initial shutter closing signal which is outputted at the same time as the synchro switch 21 is turned on. In addition, an entire operation period signal is turned on.

After a relatively short time, the initial shutter closing signal falls and, at the same time, the light source shutter 142 begins to open.

At this time, the brightness (luminous flux) B of the illuminating light supplied to the endoscope, which is determined by the brightness of light from the light source 140 and the degree of opening of the diaphragm 143, is maintained at the illuminating light flux $B_0$ in the observational state, and as the light source shutter 142 opens, the integral output voltage from the photometric circuit 116 begins to rise.

The CPU 151 detects a rate of change (differential) of the integral output voltage V per unit time, $dV/dt = c \cdot V_a/t_a$, in a very short period of time, $dt = t_a - t_0 = t_a$, which begins at the time ($t_0 = 0$) when the light source shutter 142 begins to open, and calculates an expected exposure T' from the detected value. In the above expression, $V_a$ is an integral output voltage at $t_a$, and c is a correction coefficient which is greater than 1.

The calculation of the expected exposure time T' is based on a set voltage $V_r$, which is automatically set in accordance with an exposure index that is inputted through the exposure index setting switch 145. Specifically, the expected exposure time T' is calculated as follows:

$$T' = (V_r - V_a) dt/dV + t$$

In this embodiment, three different kinds of reference exposure time, that is, $T_1$, $T_2$ and $T_3$, are set. These reference exposure times in a preferred embodiment are as follows:
$T_1 = 0.01$ sec
$T_2 = 0.015$ sec
$T_3 = 0.03$ sec The illuminating light flux B is controlled by controlling either one or both of the light source 140 and the diaphragm 143 as follows:
① when $T' < T_1$, $B = B_0/3$
② when $T_1 \leq T' < T_2$, $B = B_0$
③ when $T_2 \leq T' < T_3$, $B = 3B_0/2$
④ when $T_3 \leq T'$, B = maximum By controlling the illuminating light flux B in this way, the exposure time can be controlled so as to fall within an ideal range, that is, from $T_1$ to $T_3$, which in a preferred embodiment may be from 0.01 sec to 0.03 sec, on almost all occasions.

Figure 6B:
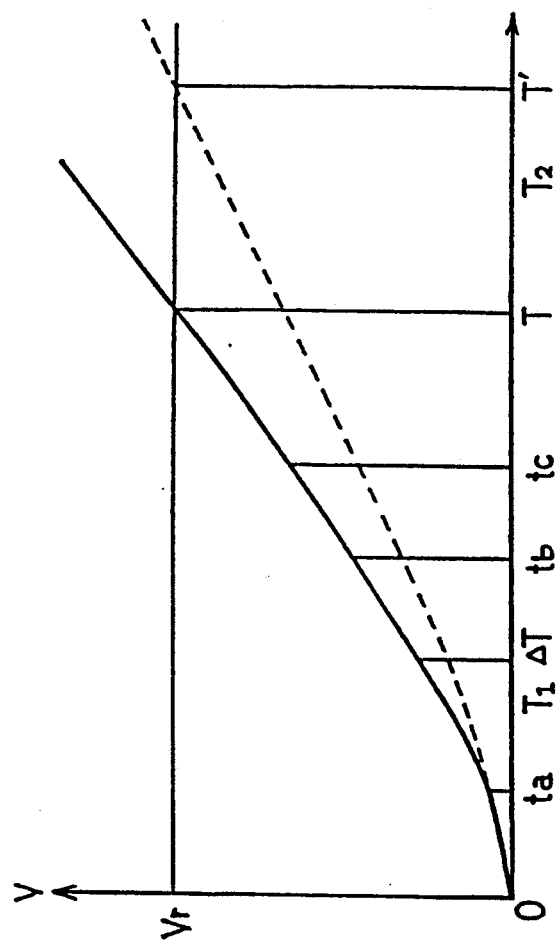
FIGS. 6a and 6b are graphs showing the operation of the second embodiment.
Figure 6A:
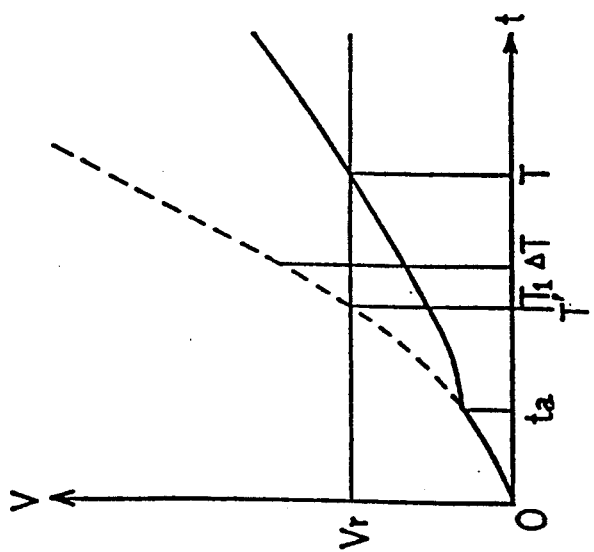

FIG. 6a shows a control operation in the case of ①, in which, since the expected exposure time T' is too short, the illuminating light flux B is reduced to one third of the observational value so that the exposure time T falls within the ideal range. The chain line shows the result that is obtained when the control of the light quantity according to the present invention is not carried out, and the solid line shows the result that is obtained when the light quantity is controlled according to the present invention.

FIG. 6b shows a control operation in the case of ③, in which, since the expected exposure time T' is within the ideal range but relatively long, the illuminating light flux B is increased to 1.5 times the observational value so that the exposure time T becomes a relatively short period of time within the ideal range. The chain line shows the result that is obtained when the control of the light quantity according to the present invention is not carried out, and the solid line shows the result that is obtained by controlling the light quantity according to the present invention.

To increase the degree of accuracy of the above-described control, it is preferable to differentially detect the integral output again when the light source shutter 142 is fully opened, and to calculate an expected exposure time to effect the control of the luminous flux B of the illuminating light that is supplied to the endoscope once again. This is due to the following reasons. In the control that is effected immediately after the starting point $t_0$, since the light source shutter 142 is beginning to open, the rise of the integral output voltage V is not linear relative to time and hence dV/dt is not definite, and the value of dV is so small that a computational error is likely to occur.

For these reasons, a point of time $t_b$ at which at least the time $\Delta T$ required for the light source shutter 142 to open fully has elapsed since $t_0$ is defined as a next starting point, and a rate of change of the integral output voltage V per unit time is detected for a predetermined short time $(t_c - t_b)$. Then, the remaining exposure time $T_x$ at $t_c$ is calculated as follows:

$$T_x = (V_r - V_c) dt/dV$$

where $V_c$ is an integral output voltage at $t_c$.

Assuming that the interval of time between $t_c$ and $T_3$ is represented by $T_4$, if $T_x > T_4$, that is, if the total exposure time is greater than $T_3$, which in a preferred embodiment is 0.03 sec, the illuminating light flux B is maximized.

When the entire operation period signal turns off after the exposure time control has been effected in this way, the system returns to the state before the photographing operation, that is, the observational state.

Figure 7A:
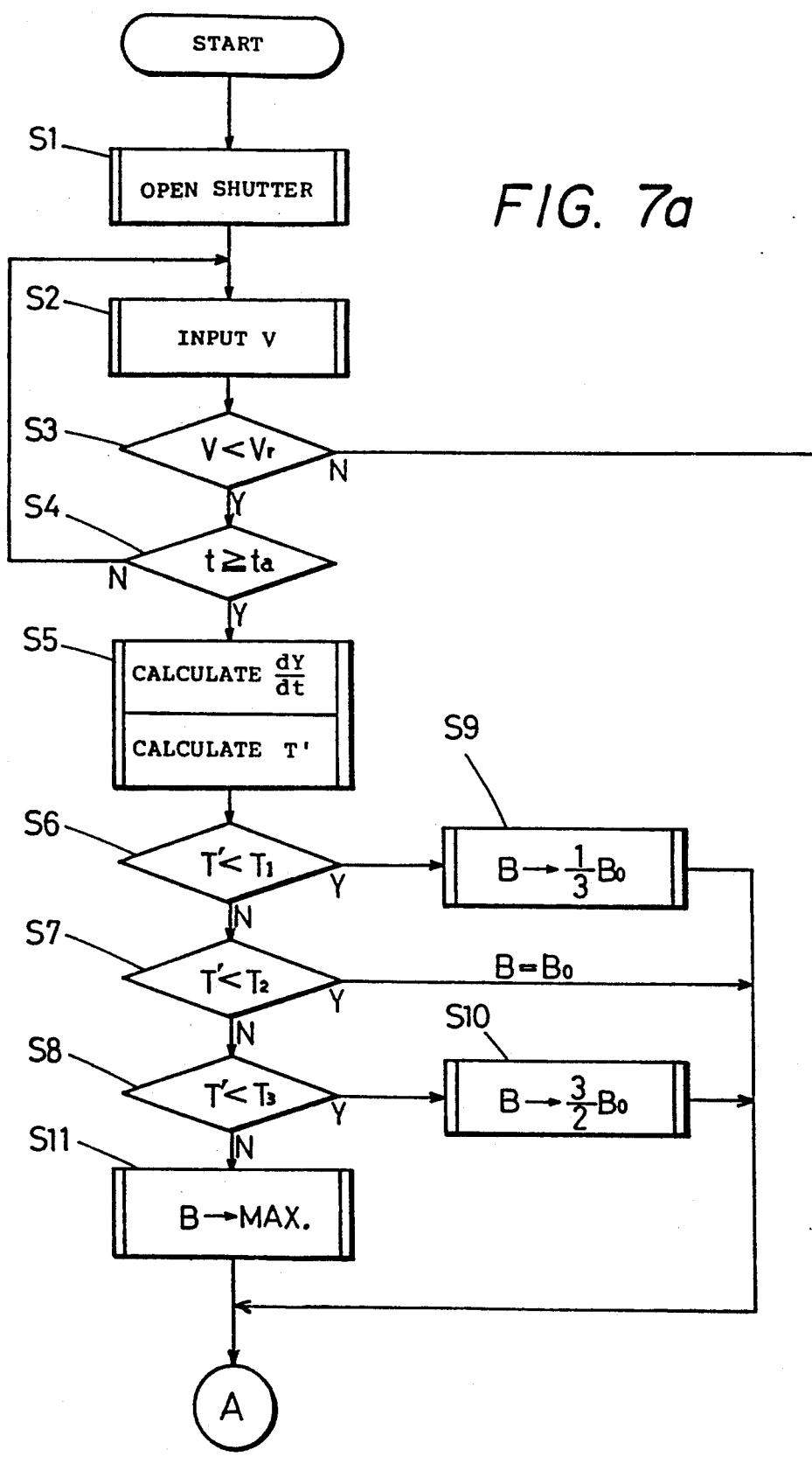
FIGS. 7a to 7d are flowcharts showing the control process of the second embodiment.
Figure 7B:
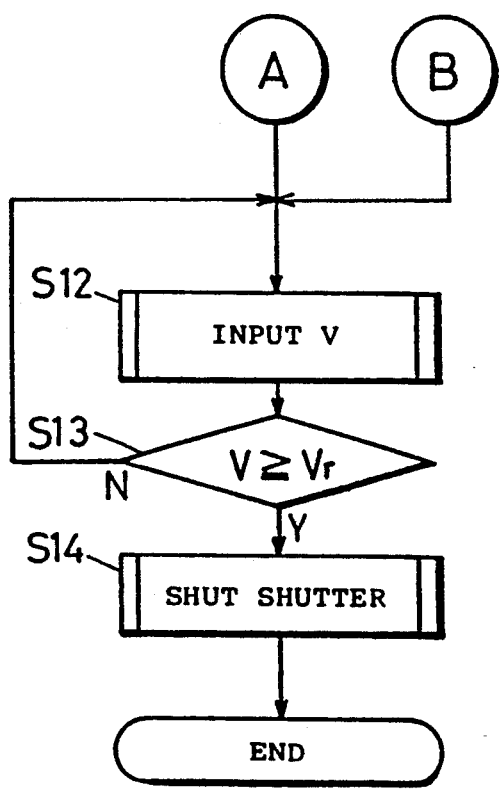

FIGS. 7a to 7d are flowcharts showing the control process that is executed in the controller 150 to effect the above-described control. Specifically, FIGS. 7a and 7b show the control process in which the control of the luminous flux B of the illuminating light is effected only once. In these figures, S denotes Steps.

This process starts in response to a fall of the initial shutter closing signal. The light source shutter 142 is opened in S1. At the same time as the shutter 142 begins to open, an integral output voltage V is inputted from the photometric circuit 116 in S2. If V is judged to be smaller than the set voltage $V_r$ in S3, it is then judged in S4 whether or not the time t elapsed since the beginning of the opening of the light source shutter 142 has reached a predetermined time $t_a$.

If t has not yet reached $t_a$, the process returns to S2, in which a new integral output voltage V is inputted. If it is judged in S3 that V has exceeded the set voltage $V_r$, the process proceeds to S12, and the light source shutter 142 is closed in S14, thus completing the control process. If it is judged in S4 that the elapsed time t has reached $t_a$, the process proceeds to S5, in which $dV/dt = c \cdot V_a/t_a$ and $T' = (V_r - V_a)dt/dV + t_a$ are successively calculated.

T' is compared with $T_1$, $T_2$ and $T_3$ in S6, S7 and S8. If $T' < T_1$ in S6, the illuminating light flux B is reduced to one third of the observational value in S9. If $T' < T_2$ in S7, B is maintained at $B_0$. If $T' < T_3$ in S8, $B = 3B_0/2$ is set in S10, whereas, if NO is the answer (i.e., if $T' \geq T_3$) in S8, the illuminating light flux B is maximized.

With the illuminating light flux B controlled at an optimal value in this way, the integral output voltage V is inputted in S12, and it is judged in S13 whether or not V has reached the set voltage $V_r$. If NO, the process returns to S12 to repeat the same operation. When the integral output voltage V reaches the set voltage $V_r$, the light source shutter 142 is closed in S14, thus completing the control process.

Figure 7C:
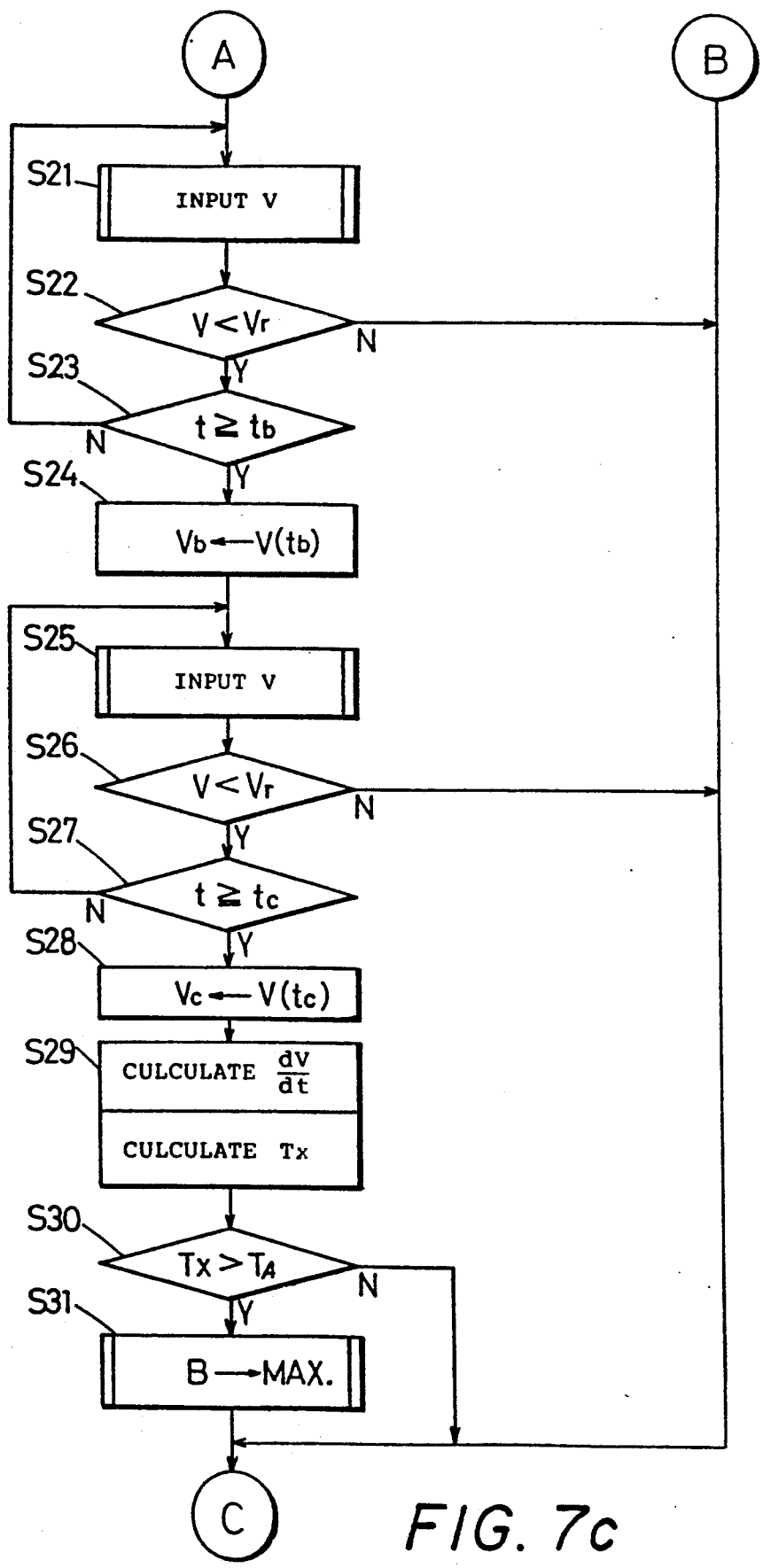
Figure 7D:
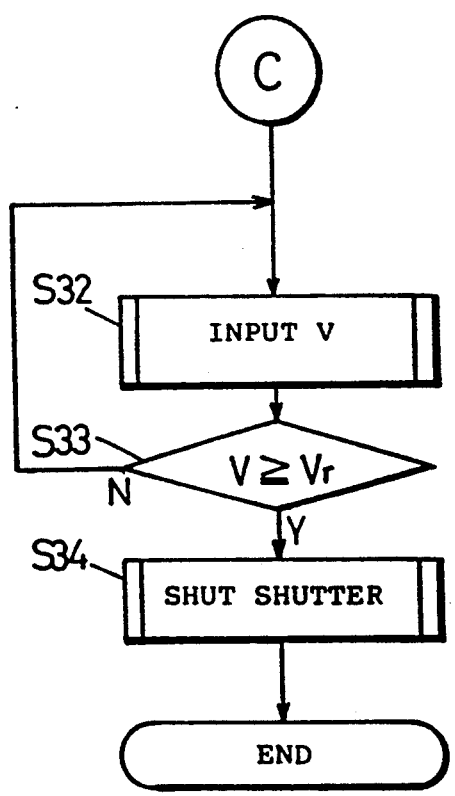

FIGS. 7c and 7d are flowcharts showing a control process in which the second control is effected after the light source shutter 142 is fully opened, the control process being executed, following the flow that is shown in FIG. 7a.

After the first control has been completed, an integral output voltage V is inputted from the photometric circuit 116 in S21. If V is judged to be smaller than the set voltage $V_r$ in S22, it is then judged in S23 whether or not the elapsed time t has reached $t_b$.

If t has not yet reached $t_b$, the process returns to S21, in which a new integral output voltage V is inputted. If it is judged in S22 that V has exceeded the set voltage $V_r$, the process proceeds to S32, and the light source shutter 142 is closed in S34, thus completing the control process. If it is judged in S23 that t has reached $t_b$, the integral output signal at the time when $t = t_b$ is stored as $V_b$ in S24.

In S25 to S28, the integral output voltage at the time when $t = t_c$ is stored as $V_c$, in the same way as in S21 to S24. Then, $dV/dt = (V_c - V_b)/(t_c - t_b)$ and $T_x = (V_r - V_c)dt/dV$ are successively calculated in S29.

Once calculated, $T_x$ is compared with $T_4$ in S30. If $T_x$ is not greater than $T_4$, the illuminating light flux B is left unchanged, whereas, if $T_x > T_4$, the illuminating light flux B is maximized.

With the illuminating light flux B recontrolled in this way, the integral output voltage V is inputted in S32, and it is judged in S33 whether or not V has reached the set voltage $V_r$. If V has not reached $V_r$, the process returns to S32 to repeat the same operation. When the integral output voltage V reaches the set voltage $V_r$, the light source shutter 142 is closed in S34, thus completing the control process.

Although in the foregoing embodiment the illuminating light flux B is controlled at four optional levels, including the illuminating light flux $B_0$ at the time of the observation, the number of levels for the illuminating light flux B may be selected as desired. The second control is not always needed, on the other hand, the light quantity control may be effected three or more times.

According to the present invention, the luminous flux of the illuminating light that is supplied from the light source device to the endoscope is controlled so that the exposure time for photography falls within a preset range. It is therefore possible to carry out photography with an ideal exposure time at all times and hence possible to prevent both over-exposure and blur. Thus, high-quality photography can be stably and reliably carried out.

While the invention has been described by reference to a specific embodiment chosen for purposes of illustration, it should be apparent that numerous modifications could be made thereto by those skilled in the art without departing from the basic concept and scope of the invention.

We claim:

1. A photographing light quantity controller for an endoscope, which is used to control the quantity of illuminating light when a photograph is to be taken through said endoscope, comprising:
    means for photoelectrically converting a brightness level of the reflected light from an object, which is illuminated with a light source, into an electric signal and outputting said electric signal;
    means for integrating an output from said photoelectric conversion means and outputting an integral value;

means for differentially detecting and outputting a rise of a signal representative of an integral value which is outputted from said integration means; and means for controlling the brightness of illuminating light wherein, when the output from said detecting means is greater than a first reference value, the brightness of light that illuminates said object is controlled to a relatively low level, and wherein, when the output from said detecting means is less than a second reference value which is less than said first reference value, the brightness of said illuminating light is controlled to a relatively high level, and when the output from said detecting means is between said first and second reference values, the brightness of said illuminating light is controlled to a predetermined level between said two brightness levels.

2. A photographing light quantity controller according to claim 1, further comprising a shutter which is capable of intercepting the light path of said illuminating light, and a shutter control means for controlling the operation of said shutter.

3. A photographing light quantity controller according to claim 2, wherein said shutter control means closes said shutter when the output from said integration means rises to a preset value.

4. A photographing light quantity controller according to claim 1, wherein said illuminating light brightness control means effects control such that, when the output from said detecting means is higher than said first reference value, the brightness of light that illuminates said object is controlled to a minimum level within a variable range, whereas, when the output from said differentiation means is less than said second reference value, the brightness of said illuminating light is controlled to a maximum level within said variable range.

5. A photographing light quantity controller according to claim 4, wherein the brightness of light that illuminates said object is controlled by varying the brightness of light that is emitted from said light source.

6. A photographing light quantity controller according to claim 1, wherein said endoscope is further comprising a means for transmitting an image of said object, said photoelectric converting means adapted to receive light that is transmitted by said image transmitting means.

7. A photographing light quantity controller according to claim 2, wherein said endoscope is further comprising an illuminating light transmission means for leading illuminating light that is emitted from said light source to said object, said shutter adapted to be located between said light source and a light incident end of said illuminating light transmission means.

8. A photographing light quantity controller for an endoscope, which is used to control the quantity of illuminating light when a photograph is to be taken through said endoscope, comprising:

means for photoelectrically converting a brightness level of the reflected light from an object, which is illuminated with a light source, into an electric signal and outputting said electric signal; means for detecting a rate of change per unit time of the quantity of exposure light immediately after photography beings from said electric signal that is inputted thereto from said photoelectric conversion means, and outputting a rate signal representative of the detected rate of change; and means for making a comparison between said rate of change that is represented by said rate signal outputted from said rate change detecting means and a plurality of reference values and controlling the brightness of said illuminating light in accordance with a result of the comparison.

9. A photographing light quantity controller for an endoscope, which is used to control the quantity of illuminating light when a photograph is to be taken through said endoscope, and wherein the quantity of illuminating light may be set at an observation level, comprising:

means for photoelectrically converting a brightness level of exposure light that is applied in a photographing device after being reflected from an object, which is illuminated with a light source, into an electric signal and outputting said electric signal;

means for integrating said electric signal from said photoelectric converting means and outputting an integral output value;

means for detecting a rate of change per unit time of integral output values rom said integration means and calculating an expected exposure time from a detected rate of change value; and control means which is activated by an output from said expected exposure time calculating means to control the brightness of illuminating light that is supplied from said light source to said endoscope such that the exposure time falls within a predetermined range;

wherein said control means compares said expected exposure time with at least first and second reference exposure times, whereby when said expected exposure time is shorter than said first reference exposure time, the brightness of illuminating light is controlled to be at a lower level than said observation level, and when said expected exposure time is between said first and second reference exposure times, the brightness of illuminating light is controlled to be at substantially the same level as said observation level, and when said expected exposure time is longer than said second reference exposure time, the brightness of illuminating light is controlled to be at a higher level than said observation level.

10. A photographing light quantity controller according to claim 9, further comprising a shutter which is capable of intercepting the light path of said illuminating light, and a shutter control means for controlling the operation of said shutter.

11. A photographing light quantity controller according to claim 10, wherein said shutter control means closes said shutter when the integral output valve from said integration means rises to a preset value.

12. A photographing light quantity controller according to claim 9, wherein the detection of a rate of change per unit time and the calculation of an expected exposure time, executed by said expected exposure time calculating means, are performed a plurality of times in a single photographing operation, and further wherein the control of the brightness of the illuminating light that is correspondingly supplied to said endoscope is effected a plurality of times in a single photographing operation correspondingly.

13. A photographing light quantity controller according to claim 9, wherein the brightness of light that illuminates said object is controlled by varying the brightness of light that is emitted from said light source.

14. A photographing light quantity controller according to claim 9, wherein the brightness of light that illuminates said object is controlled by a diaphragm which is capable of varying an area of passage of the illuminating light that is emitted from said light source.

15. A photographing light quantity controller according to claim 9, wherein said endoscope is provided with a means for transmitting an image of said object, said photoelectric converting means adapted to receive light that is transmitted by said image transmitting.

16. A photographing light quantity controller according to claim 9, wherein said endoscope is provided with an illuminating light transmission means for leading illuminating light that is emitted from said light source to said object, said shutter adapted to be located between said light source and a light incident end of said illuminating light transmission means.

17. A photographing light quantity controller for an endoscope, which is used to control the quantity of illuminating light when a photograph of an object is to be taken through said endoscope, comprising:

means for detecting a brightness level of reflected light from an object, which is illuminated with a light source and means for controlling the brightness of illuminating light in such a manner that, when a first brightness level detected by said detecting means is higher than a first reference value, the brightness of light that illuminates said object is controlled to a relatively low level, whereas, when a second brightness level detected by said detecting means is lower than a second reference value, which is smaller than said first reference value, the brightness of said illuminating light is controlled to a relatively high level, and when the output from said detecting means is between said first and second reference values, the brightness of said illuminating light is controlled to a predetermined level between said first and second brightness levels.

18. A photographic light quantity controller according to claim 9, wherein the exposure light is applied to a photographic plane in said photographing device after being reflected from the object, and said exposure time falls into said predetermined range at said photographic plane.

* * * * *

UNITED STATES PATENT AND TRADEMARK OFFICE
CERTIFICATE OF CORRECTION

PATENT NO. : 5,115,261
DATED : May 19, 1992
INVENTOR(S) : Nobuhiro NODA et al.

It is certified that error appears in the above-indentified patent and that said Letters Patent is hereby corrected as shown below:

At column 11, line 31 (claim 4, line 4) of the printed patent, change "higher" to ---greater---.
At column 11, line 35 (claim 4, line 8) of the printed patent, change "differentiation" to ---detecting---.
At column 12, line 50 (claim 10, line 4) of the printed patent, delete "the".
At column 12, line 63 (claim 12, line 8) of the printed patent, delete "correspondingly".
At column 12, line 64 (claim 12, line 9) of the printed patent, insert ---correspondingly--- before "effectively".
At column 12, line 65 (claim 12, line 10) of the printed patent, delete "correspondingly".

Signed and Sealed this

Nineteenth Day of April, 1994

*Attest:*

BRUCE LEHMAN

*Attesting Officer*   *Commissioner of Patents and Trademarks*